United States Patent [19]

Pinel et al.

[11] Patent Number: 5,762,495
[45] Date of Patent: Jun. 9, 1998

[54] SURGICAL INSTRUMENT PARTICULARLY FOR DENTAL SURGERY

[75] Inventors: Alain Pinel, Martignas/Jalles; Pascal Dupeyron; Francis Dieras, both of Bordeaux, all of France

[73] Assignee: Satelec S.A., Merignac, France

[21] Appl. No.: 571,827

[22] PCT Filed: Jun. 29, 1994

[86] PCT No.: PCT/FR94/00791

§ 371 Date: Dec. 26, 1995

§ 102(e) Date: Dec. 26, 1995

[87] PCT Pub. No.: WO95/01136

PCT Pub. Date: Jan. 12, 1995

[30] Foreign Application Priority Data

Jun. 29, 1993 [FR] France .................... 93 07921
Jan. 14, 1994 [FR] France .................... 94 00385

[51] Int. Cl.⁶ .................................................. A61C 1/07
[52] U.S. Cl. ....................... 433/86; 433/84; 433/126
[58] Field of Search ............................... 433/126, 118, 433/119, 120, 115, 84, 85, 87

[56] References Cited

U.S. PATENT DOCUMENTS

| 3,518,766 | 7/1970 | Burt | 433/119 |
| 4,080,737 | 3/1978 | Fleer | 433/126 |
| 4,382,786 | 5/1983 | Lohn et al. | 433/126 X |
| 4,589,847 | 5/1986 | Loge et al. | 433/126 |
| 4,634,420 | 1/1987 | Spinosa et al. | 433/119 X |
| 4,804,364 | 2/1989 | Dieras et al. | 433/119 X |
| 5,312,349 | 5/1994 | Lohn | 433/126 X |
| 5,482,462 | 1/1996 | Rosenstatter | 433/126 |

*Primary Examiner*—Nicholas D. Lucchesi
*Attorney, Agent, or Firm*—Young & Thompson

[57] ABSTRACT

A surgical instrument including an operative assembly (1) and a supply assembly (3). The back of the operative assembly (1) and the front of the supply assembly (3) have complementary connectors forming a sealed connection between the assemblies. The supply assembly (3) comprises at least one duct (43) for feeding a first fluid as far as the connectors. The surgical instrument is characterized in that it comprises a member (31) for sealing the fluid duct (43) when the operative assembly (1) is connected to the supply assembly (3), and the operative assembly (1) includes a member (25) for feeding at least one second fluid.

12 Claims, 3 Drawing Sheets

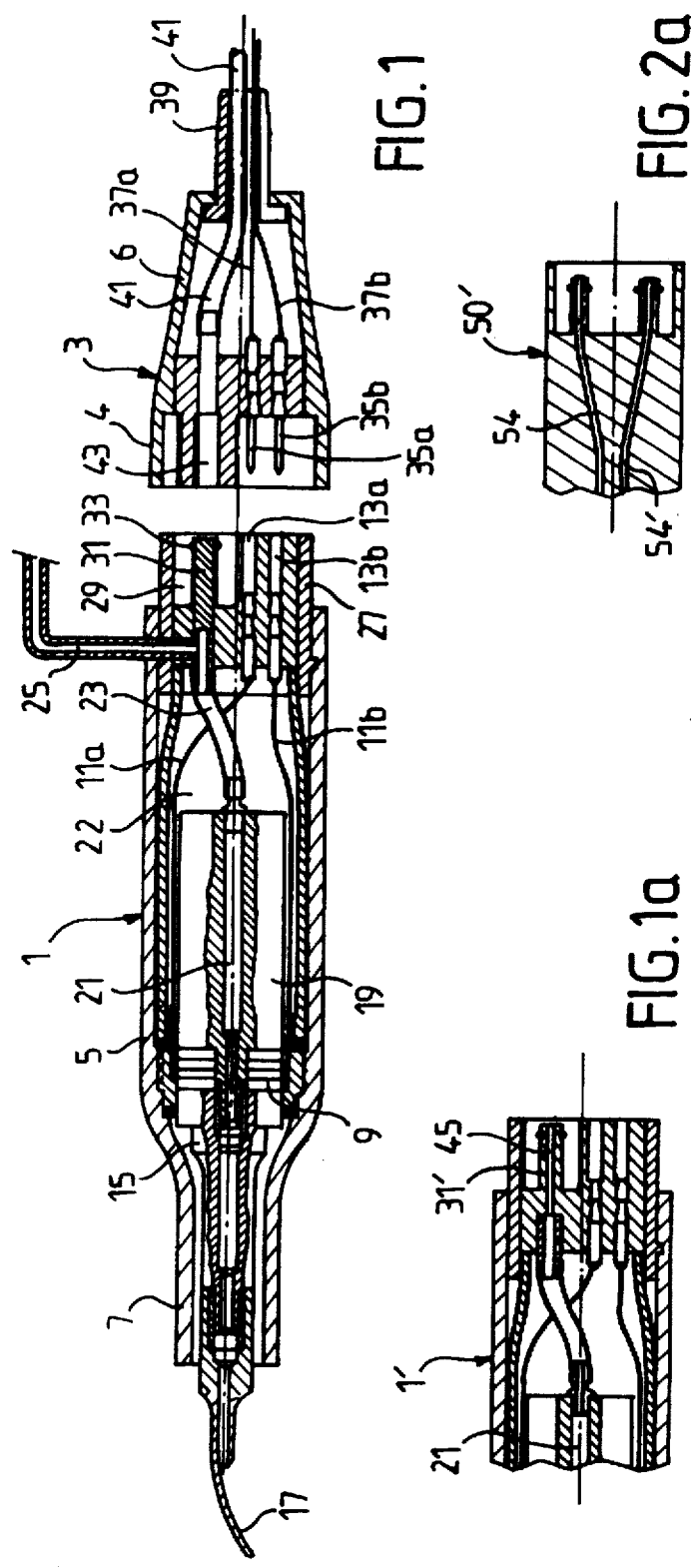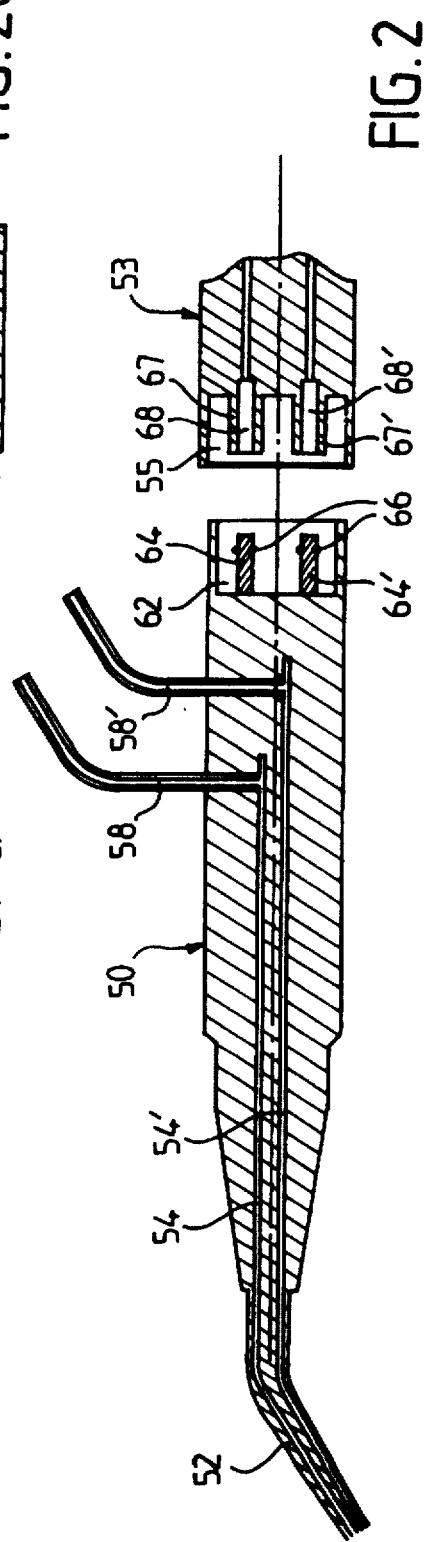

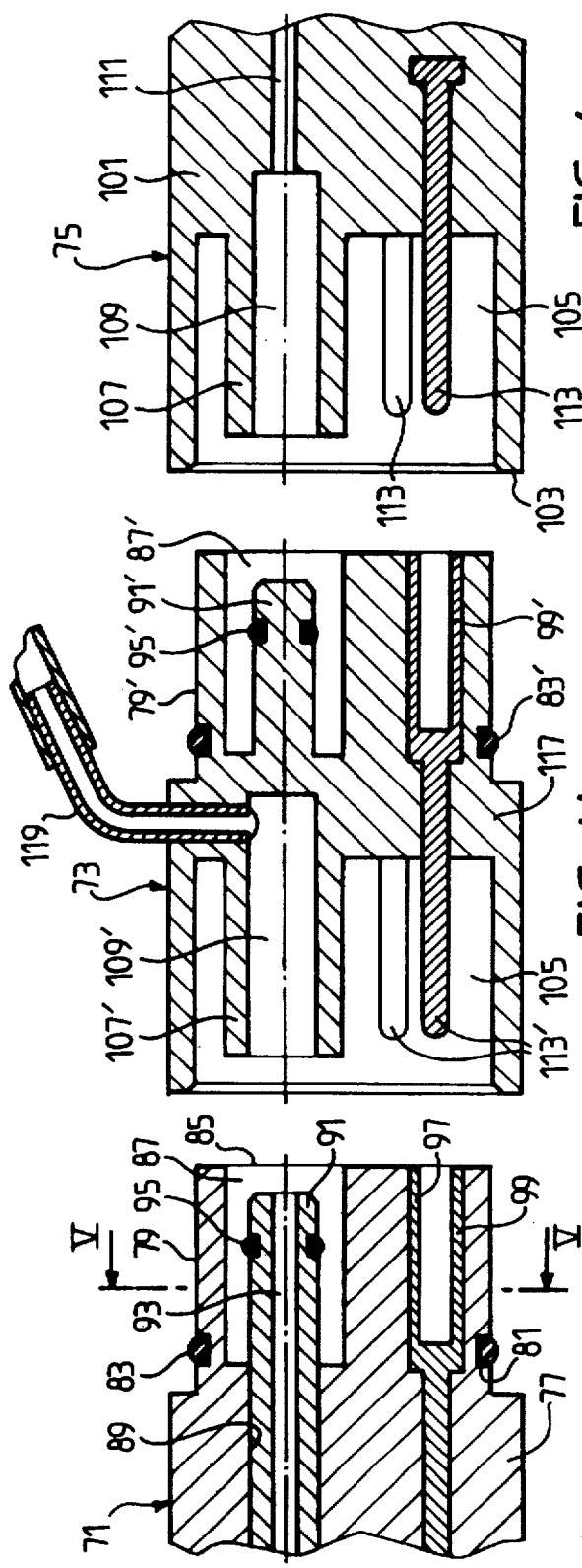
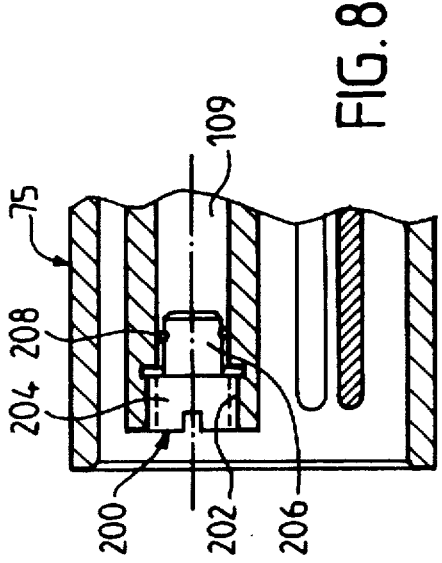
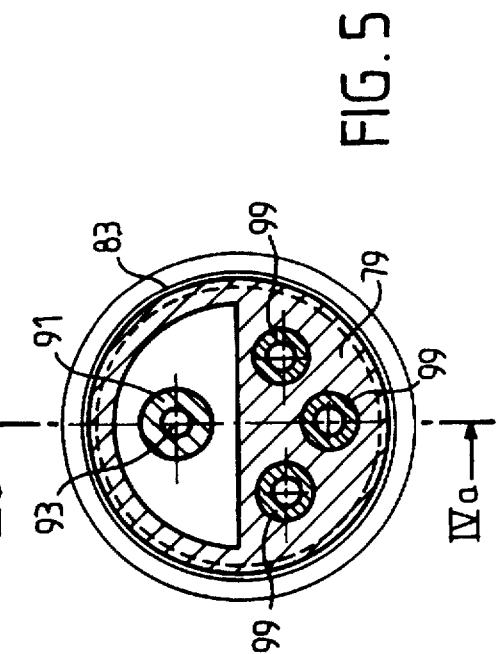

SURGICAL INSTRUMENT PARTICULARLY FOR DENTAL SURGERY

FIELD OF THE INVENTION

The present invention relates to a surgical instrument, particularly for dental surgery, and more particularly to a surgical instrument supplied with at least one sterile fluid.

BACKGROUND OF THE INVENTION

Instruments used in dental surgery, such as those using for example ultrasound, ordinarily require, on the one hand, an energy supply, namely either electrical energy or energy furnished by a gas under pressure and, on the other hand, a supply of liquid such as an irrigation liquid.

It is known that certain periodontal procedures use this type of instrument, and particularly those taking place between the gum and the tooth of a patient, such as procedures on the radicular surface, must be carried out with sterile instruments and irrigation fluids. If the existing odontological instruments permit easily and rapidly replacing a tool-carrying element, or handpiece, which is non-sterile, with a sterile tool-carrying element, they do not permit on the other hand exchanging with the same facility the irrigation fluid which supplies this instrument to replace it with a sterile fluid. In current practice, the surgeon having begun a procedure in a non-sterile mode and wishing to carry it on in a sterile mode is thus constrained to change all of his instruments, which represents for him a supplemental difficulty.

SUMMARY OF THE INVENTION

The present invention has for its object to provide means permitting the surgeon to change easily and substantially instantaneously, from one non-sterile configuration to a sterile configuration, or from a given irrigation liquid to another irrigation liquid.

The present invention thus has for its object a surgical instrument and particularly a surgical instrument supplied with at least one sterile fluid, comprising an active element and a supply element, the rear portion of the active element and the front portion of the supply element comprising complementary connection means permitting ensuring their interconnection in a sealed manner, the supply element comprising at least one supply channel for a first fluid, opening adjacent the connection means, characterized in that:

it comprises means ensuring closure of said supply channel for the first fluid, when the active element is connected to the supply element.

the active element comprises means for supply of at least one second fluid.

In one embodiment of the invention, the means ensuring closure of said supply channel for the first fluid, when the active element is connected to the supply element, are an integral portion of the rear portion of the active element.

In another embodiment of the invention, the active element is constituted by at least two elements interconnectable in a sealed manner, namely a forward or head element, and a rear or irrigation connector element, the supply means for the second fluid are connected to the irrigation connector, and the rear portion of the head comprises sealed connection means adapted to be connected with the supply element, the supply channel for the first fluid being in communication with the head when this latter is connected to the supply element.

In another particularly interesting embodiment of the invention, the active element is constituted by at least two elements interconnectable in a sealed manner, namely a forward or head element, and a rear or irrigation connector element, the supply means for at least a second fluid are in communication with the irrigation connector, and the rear portion of the head comprises connection means complementary to those of the supply element permitting ensuring a sealed connection with the latter, the supply channel for the first fluid being in communication with the head when this latter is connected to the supply element.

The present invention can be embodied in numerous existing apparatus, and thus permits the practitioner to change simply and substantially instantaneously from one nonsterile configuration to a sterile configuration and, more generally, to use in the course of a single procedure several irrigation liquids which may or may not be mixed and which moreover are available in a substantially immediate fashion.

BRIEF DESCRIPTION OF THE DRAWINGS

There will be described hereinafter, by way of nonlimiting example, several embodiments of the present invention, with reference to the accompanying drawing in which:

FIG. 1 is a view in axial cross section of a detartarer according to the invention.

FIG. 1a is a fragmentary axial cross-sectional view of the handpiece of a detartarer according to the prior art.

FIG. 2 is a view in axial cross section of a dental syringe according to the invention.

FIG. 2a is a fragmentary axial cross-sectional view of a dental syringe according to the prior art.

FIG. 4a is a fragmentary axial cross-sectional view of a tool-carrying element, or handpiece, of a surgical instrument adapted for odontological procedures.

FIG. 4b is an axial cross-sectional view on the line IVb—IVb of FIG. 5, of an irrigation connector, adapted to be connected to the rear portion of the handpiece shown in FIG. 4a, so as to constitute an active element.

FIG. 4c is a fragmentary axial cross-sectional view of a supply element adapted to be connected to the rear portion, either of the handpiece shown in FIG. 4a, or of the irrigation connector shown in FIG. 4b.

FIG. 5 is a transverse cross-sectional view of the handpiece shown in FIG. 4a on the line V—V of the latter.

FIGS. 6, 7 and 8 are fragmentary views, in axial cross section, of three modified embodiments of the invention.

DETAILED DESCRIPTION OF THE PREFERRED EMBODIMENTS

Figure 3:
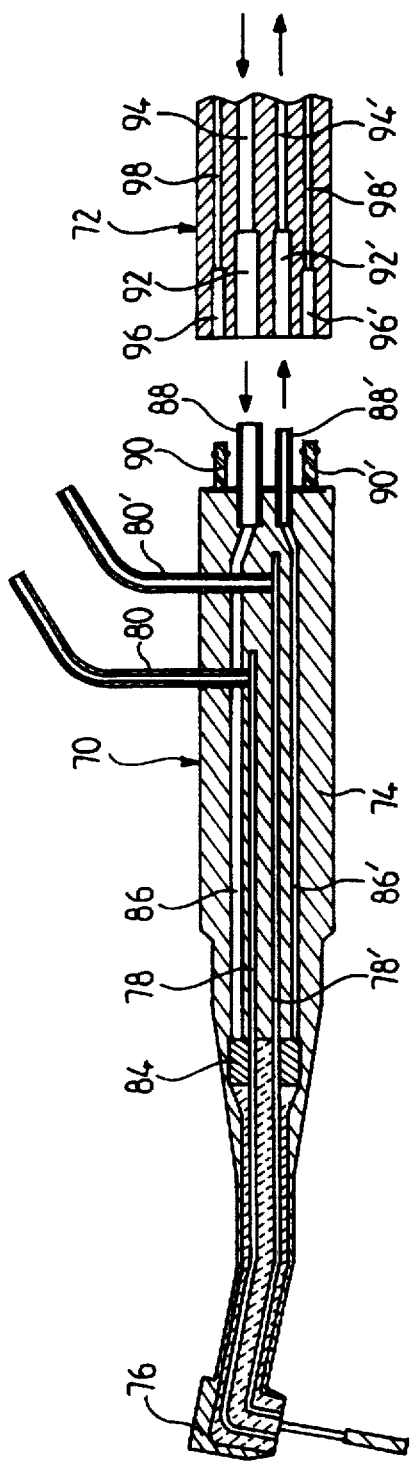
FIG. 3 is an axial cross-sectional view of a dental drill according to the invention.

In a first embodiment of the invention, shown in FIG. 1, the surgical instrument is constituted by a detartarer device. This detartarer device is comprised by an active element formed by a handpiece 1 adapted to be connected to a supply element 3. The handpiece 1 is constituted by a hollow cylindrical body 5, made of an insulating material, which terminates in its forward portion in a hollow cylindrical portion 7 of smaller diameter. The body 5 encloses in known fashion piezo-electric wafers 9 whose end portions are respectively connected, by electrical supply conductors 11a, 11b, to female plugs 13a, 13b opening toward the rear portion of the handpiece 1.

A vibration amplifier 15 is in contact with the forward surface of the piezo-electric wafers 9, this amplifier 15 terminating in an insert 17 subjected to longitudinal vibratory movement when the piezo-electric wafers 9 are supplied with high frequency alternating current.

The rear portion of the piezo-electric wafers 9 is in contact with a counter-mass 19. This latter is pierced by an axial channel 21 which opens on its rear surface in a cavity 22 of the body 5 and which is forwardly prolonged through the amplifier 15 to adjacent the insert 17. The inlet of the channel 21 is in communication through a flexible tube 23 with a rigid radial elbowed tube 25, which is secured to the body 5 and which is adapted to be connected particularly to a source of sterile liquid under pressure (not shown in the drawing).

The rear portion of this handpiece 1 terminates in a cylindrical rear end 27, constituted by an insulating material, which is fixed and engaged in the extreme forward end of the body 5. The rear end 27 receives the two female plugs 13a and 13b, and is rendered hollow by a cylindrical cavity 29 of semi-circular transverse cross section, traversed by a longitudinal cylindrical closure plug 31 which terminates at its end in a toric sealing joint 33.

The supply element 3 is comprised essentially of a cylindrical forward portion 4, of an internal diameter substantially equal to the external diameter of the rear end 27, and a truncated conical end portion 6. The forward surface of the supply element 3 comprises different cavities and bosses complementary to the rear portion of rear end 27, such that the supply element 3 can connect and become lodged in this latter. The forward portion of the supply element 3 thus comprises essentially two male pins 35a, 35b, adapted to be received respectively in the female plugs 13a and 13b of the rear end 27. These male pins 35a, 35b are connected to wires 37a, 37b for high-frequency alternating current supply, which are disposed in a sleeve 39 which connects the rear portion of the supply element 3 to a current generator, not shown in the drawing. Within the sleeve 39 is also disposed a channel 41, connected to an inlet for water under pressure (not shown in the drawing), and which opens into a cylindrical cavity 43 opening on the forward portion of the supply element 3, opposite the closure plug 31, when the handpiece 1 is ready to be connected to the supply element 3. Under these conditions, when the supply element 3 is connected to the handpiece 1, the closure plug 31 is engaged in the cavity 43 whose closure it ensures, and the male pins 35a, 35b are located in the female plugs 13a, 13b, thus ensuring the electrical connection of the piezo-electric wafers 9 with the current generator. Moreover, in this connection position, the closure plug 31 closing the inlet for water under pressure from the channel 41, the supply of liquid of the handpiece 1 is then via the elbowed tube 25, connected for this purpose to an external supply particularly of sterile liquid.

The supply element 3 can thus be connected to several types of handpieces, namely conventional handpieces, which is to say according to the prior art, and to handpieces according to the invention.

By way of comparison, there is shown in FIG. 1a the rear portion of a handpiece 1' of conventional type according to the prior art. This handpiece 1' comprises no elbowed supply tube for a second irrigation liquid and the closure plug is replaced by an element 31' rendered hollow by a longitudinal supply channel 45 which places in communication, via the channel 41, the axial channel 21, opening into the forward portion of the detartarer, with the supply channel for the first irrigation liquid.

Thus, when a handpiece 1', of conventional type, is connected to the supply channel 3, the supplies of irrigation liquid and electrical energy of this latter take place via the supply element 3 whilst, when a handpiece 1 according to the invention is connected to this same supply element 3, the irrigation liquid supply takes place via the elbowed tube 25 connected, for example, to sterile liquid supply means, whilst the electrical supply still takes place via the supply element 3.

Under these conditions, when the practitioner desires to change from a non-sterile configuration to a sterile configuration, it suffices for him to exchange one handpiece 1' of conventional type, for a handpiece 1 according to the invention, and to connect this latter to sterile liquid supply means.

The present invention can also be practiced with other types of surgical apparatus and particularly, as shown in FIG. 2, with a dental syringe.

In this FIG. 2, the dental syringe is connected by an active element or body 50, and by a supply element 53. The cylindrical body 50 terminates in known fashion in an elbowed tip 52. This tip 52, as well as the body 50, is traversed by two respective longitudinal channels 54, 54' opening through the end of the tip 52, and each of these channels is connected at its internal end to an elbowed radial tube 58, 58' secured to the body 50 of the syringe and projecting from this body. The rear portion of the body 50 is rendered hollow by a cylindrical cavity 62 opening inwardly, which encloses two longitudinal closure plugs 64, 64' constituted by two cylindrical pins each provided with a toric sealing joint 66.

The body 50 of the dental syringe is adapted to be connected to the supply element 53, whose forward portion is rendered hollow for this purpose by a cylindrical cavity 55, of an internal diameter substantially equal to the external diameter of the body 50, and whose rear comprises two projecting longitudinal bosses 67, 67' each rendered hollow by a longitudinal channel 68, 68' of an internal diameter substantially equal to that of the closure plugs 64, 64', so as to be able to receive these latter when the body 50 is connected to the supply element 53. The channels 68, 68' are respectively connected to supply means for liquid and air under pressure, not shown in the drawing. When the body 50 of the dental syringe is connected to the supply element 53, the closure plugs 64, 64' ensure closure of the supply channels for liquid and air under pressure 68, 68'. The fluid supply of the syringe is then effected by elbowed tubes 58, 58', which for this purpose are connected to respective external sources for supply of sterile liquid and air under pressure, not shown in the drawing.

The supply element 53 can also receive the active elements of syringe 50' of a usual type according to the prior art, as shown in FIG. 2a. When an active element of conventional type 50' is connected to the supply element 53, the supply channels for liquid and air under pressure 68, 68' are respectively connected to the channels 54, 54' of the active element 50' of the syringe, whose tip is thus adapted to be supplied at its outlet with air and/or liquid from the supply element 53.

When the practitioner wishes to change from a nonsterile syringe mode to a sterile syringe mode, he replaces the non-sterile active element 50' of this latter with a sterile active syringe element 50 according to the invention whose supply tubes 58, 58' are respectively connected to sources of sterile liquid and air.

In a modification shown in FIG. 3, the present invention is carried out on a dental drill.

This latter is comprised by an active or tool-carrying element 70, which is adapted to be connected to a supply element 72. The overall external shape of the tool-carrying element 70 is of the type of those of the prior art. In a schematic manner, the dental drill comprises a body 74, of cylindrical shape, prolonged in its forward portion by a truncated conical portion and by a tubular element that is elbowed relative to the axis of body 74 and which supports a burr-carrying head 76. The body 74 of the tool-carrying element 70 is rendered hollow, in the longitudinal direction, by two parallel channels 78 and 78' which open at one of their ends in the burr-carrying head 76, on opposite sides of the shaft carrying the burr and, at the other end, in elbowed radial tubes 80, 80' adapted to be connected to respective sources of sterile liquid and gas, not shown in the drawing.

The body 74 comprises, substantially at the level of its truncated conical portion, a turbine 84 (shown schematically in the drawing) which is connected to a supply channel for air under pressure 86 and to an outlet channel for air 86', these channels opening at the rear end of the tool-carrying element 70, in hollow pins respectively 88 and 88' which project longitudinally from the rear end of the rear portion of the body 74. The rear portion of the body 74 is also provided with two axial closure plugs 90, 90'.

The supply element 72 is of cylindrical shape and is rendered hollow on its forward surface by two cylindrical cavities 92, 92', respectively connected by conduits 94, 94' to a source of air under pressure and to an air outlet, and which are adapted to receive respectively the hollow pins 88, 88'. The forward surface of the supply element is also rendered hollow by two cylindrical cavities 96, 96', of smaller diameter, respectively connected by conduits 98, 98' to supply means for irrigation liquid and air, and which are so positioned as to permit them to receive respectively the closure plugs 90, 90'.

The principle of operation is the same as that described above, namely that the dental drill described in FIG. 3 is usable in a sterile mode and that, in this arrangement, when the tool-carrying element 70 is connected to the supply element 72, the turbine 84 is supplied with air under pressure by means of the supply element 72, whilst the supply of sterile liquid and air takes place through elbowed tubes 80, 80', the corresponding cavities 96, 96' of the supply element 72 being then closed by the closure plugs 90, 90'. As in the case of the preceding instruments, and in an unsterile mode, the supply element can be connected to a tool-carrying element of conventional type, all the liquid supply then taking place from the supply element 72.

In one embodiment of the invention, the active element can be constituted by two elements, namely a head and an irrigation connector.

There is thus respectively shown in FIGS. 4a, 4band 4c the rear portion of a tool-carrying element of conventional type, or head 71, an irrigation connector 73 and the forward portion of a supply element 75.

The irrigation connector 73 is adapted to be connected, via its forward portion, with the rear portion of the head 71, so that these two elements, once connected, constitute the active element of the instrument. The rear portion of the irrigation connector 73 is adapted to be connected to the forward portion of the supply element 75, and the assembly of the three said elements constitutes thus a surgical instrument usable in dental treatment, particularly to scale tartar plaque which is on the teeth.

The head 71 is constituted by a cylindrical body 77 of insulating plastic material, which encloses piezo-electric wafers (not shown in the drawing) which, under the action of a high-frequency current, subject a tool or insert disposed in the forward portion of the head, to a longitudinal vibratory movement. These latter elements, of known type, are not shown in the drawing.

The head 71 terminates at its rear portion in a cylindrical portion 79 of small er diameter, which is rendered hollow by a circular peripheral groove 81 in which is received a toric sealing joint 83. The rear surface 85 of the cylindrical portion 79 of the head 71 is rendered hollow by a cylindrical chamber 87, of semi-circular transverse cross section. The bottom of the chamber 87 is itself rendered hollow by a longitudinal axis hole 89, in which is secured a metallic tube 91, provided with a central channel 93 connected to the forward end of the head 71. The rear periphery of the tube 91 is rendered hollow by a circular groove in which is received a toric sealing joint 95. The rear surface 85 of the head 71 is also rendered hollow by three cylindrical recesses 97, with longitudinal axes, in which are received three female metallic plugs 99, namely two upper side plugs and a lower central plug in FIG. 5. The upper plugs ensure the electrical connection with the piezo-electric wafers of the head 71, and the lower plug, which if desired can be connectable, enables in the present case centering with the irrigation connector 73.

The head 71 is also adapted to be connected in known manner with the supply element 75. This latter is constituted by a cylindrical body 101, of plastic material, of the same diameter as the body 77 of the head 71, and whose shape of the forward portion is complementary to that of the rear portion of the head 71. Thus, the forward surface 103 of the supply element 75 is followed by a cylindrical cavity 105, of a diameter substantially equal to that of the cylindrical portion 79, in which is formed a longitudinal cylindrical boss 107, of semi-circular transverse cross section, complementary to that of the chamber 87, and in which is provided a cylindrical recess 109 of an internal diameter substantially equal to that of the tube 91 so as to be able to receive this latter. The supply element 75 is pierced by a longitudinal channel 111, connected to supply means (not shown in the drawing) for a first irrigation liquid, which opens through the bottom of the recess 109. Three longitudinal male pins 113, complementary to the female plugs 99, project at the base of the cavity 105 and are disposed such that they can be received within the female plugs 99 of the head 71, when the supply element 75 is connected to this latter. The two upper female plugs 99 are connected to electrical supply lines.

It will be seen that once this connection is established, a first irrigation liquid, which arrives by the channel 111 of the supply element 75, can flow through the central channel 93 of the head 71, toward the forward end of this latter, and that the electric circuit of the supply element 75 is connected via male pins 113 and female plugs 99 to the head 71, and more particularly to the piezo-electric wafers.

In such configuration of known type, the practitioner is able to effect odontological operations of conventional type such as detartration of the teeth.

To effect a procedure requiring both a sterile instrument and a sterile irrigation liquid, such as for example a radicular surfacing of the tooth of a patient, the practitioner uses, according to the invention, an irrigation connector 73, such as that shown in FIG. 4b.

This irrigation connector 73 is used in the position shown in the drawing, which is to say between the head 71 and the supply element 75. To this end, it is essentially constituted by a body 117 whose forward portion is identical to the forward portion of the supply element 75 and whose rear portion is identical to the rear portion of the head 71 (the constituent elements of the forward and rear portions of the irrigation connector 73 will be designated by the same reference numerals as those used respectively for the head 71 and for the supply element 75, plus the prime sign '). The irrigation connector 73 thus comprises a cylindrical forward portion rendered hollow by a cylindrical cavity 105' opening in the front of the connector and comprising hydraulic connection means constituted by a longitudinal cylindrical boss 107' of semi-circular cross section, rendered hollow by a cylindrical recess 109' in communication with a radial channel 119 connected to supply means for at least one second irrigation liquid, and particularly a sterile irrigation liquid, and electrical connection means constituted by three male pins 113'. The irrigation connector 73 also comprises a rear cylindrical portion 79', complementary to the cylindrical cavity 105', which is rendered hollow by a semi-cylindrical cavity 87', complementary to the boss 107', from the bottom of which extends forwardly a cylindrical boss 91', complementary to the cavity 109', and which has no central channel, so as to comprise a plug and thus to close in a sealed manner the recess 109 of the supply element 75, by thus preventing the flow of the first irrigation liquid supplied by the channel 111, when the irrigation connector 73 is coupled to the supply element 75. The rear portion of the irrigation connector 73 also comprises electrical connection means constituted by three female plugs 99' complementary to the male pins 113.

Under these conditions, when the practitioner desires to effect a procedure requiring a sterile material and liquid, it suffices for him then to use an irrigation connector 73 according to the invention (sterile), connected to supply means for a sterile liquid, on a supply element 75 (non-sterile), and to secure a head (sterile) 71 onto the irrigation connector 73, which is a particularly easy and rapid operation to perform.

Figure 6:
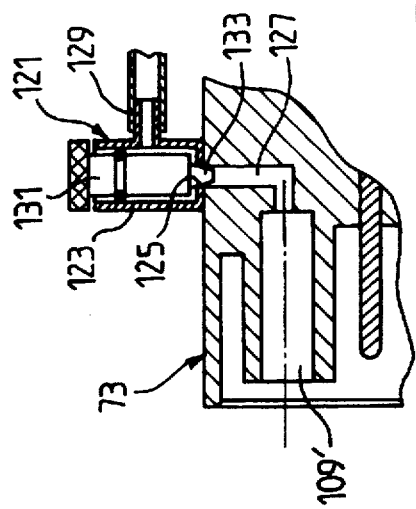

As shown in FIG. 6, the arrival of the second irrigation liquid in the handpiece or in the irrigation connector 73 can take place via a control valve 121. This latter is constituted for example by a tubular body whose bottom is provided with an orifice 125 which is in communication via a channel 127 with the recess 109' of the irrigation connector 73. The arrival of the irrigation liquid in the valve 121 takes place via a channel 129 connected to supply means for a sterile liquid, not shown in the drawing. A piston 131, which comprises a lower truncated conical portion 133 which enters the orifice 125 so as to control the flowrate and to close it more or less, is mounted in sliding sealed relation in said tubular body 123. Thus, by inserting the piston 131 more or less into the tubular body 123, the opening 125 is more or less closed and thus the flowrate of irrigation fluid admitted into the connector 73 is controlled.

The present invention permits the practitioner not only to switch rapidly from a non-sterile configuration to a sterile configuration but, by using several irrigation connectors and their associated irrigation liquids, it also permits the practitioner to use, in the course of a single procedure, several different irrigation liquids (which he could if desired mix) which he could use easily and rapidly as needed.

Figure 7:
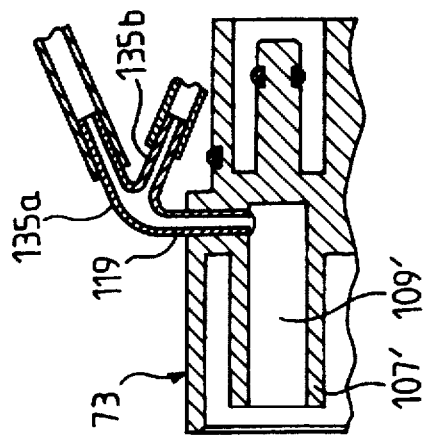

So as to facilitate the switch from one irrigation liquid to another, there can be used, as shown in FIG. 7, a channel 119 comprising several supply conduits 135a, 135b adapted to be connected to reservoirs containing different irrigation liquids. The different conduits 135a, 135b can be provided with closure means, progressive or not, which gives to the practitioner, if he desires, the possibility of mixing the various irrigation liquids and to control the proportion of their mixture admitted to the connector 73.

Preferably, the connection of the different irrigation conduits 135a, 135b takes place as close as possible to the irrigation connector 73, which gives the advantage, when it is desired to switch from a first irrigation liquid to another different irrigation liquid, not to have to evacuate more than one minimum quantity of the first irrigation liquid.

In an embodiment of the invention shown in FIG. 8, the closure of the supply channel 109 for a particular liquid, from the supply element 75, is ensured by a closure element independent from the active element, constituted by a plug 200 which is for example secured by screwing in said channel 109 before emplacement of the active element on the supply element 75. To this end, the forward portion of the latter is provided with a screw-threaded portion 202. A plug 200 comprises a screw-threaded head 204 adapted to be screwed into this screw-threaded portion 202, prolonged within the channel 109 by a portion 206 of smaller diameter provided with a toric joint 208 ensuring sealing with the internal wall of the channel 109. In a modification of the present embodiment of the invention, the closure plug could also be secured to the bottom of the irrigation channel, which permits disengaging the forward portion of this latter and permits it thus to receive the supply tubes of active elements of conventional type.

Of course, the electrical and hydraulic connection means as well as their arrangement could be of any type. There could thus be particularly used in a same element all the female connectors and on the other element all the male connectors, without departing from the scope of protection of the invention.

What is claimed is:

1. Surgical instrument adapted to be supplied by at least one sterile fluid, comprising:

an active element having a rear portion, and a supply element having a forward portion, the rear portion of the active element and the forward portion of the supply element including complementary connection means for ensuring their securement together in sealed fashion, the supply element including at least one supply channel opening adjacent the connection means, for supplying a first fluid;

said active element including supply means for supplying at least one second fluid; and means for ensuring closure of said supply channel for the first fluid, when the active element is directly connected to the supply element to stop supply of said first fluid without assisting flow of said second fluid.

2. Surgical instrument according to claim 1 wherein the means for ensuring closure of said supply channel for the first fluid, when the active element is connected to the supply element, are an integral part of the rear portion of the active element.

3. Surgical instrument according to claim 1, wherein the supply element includes energy supply means, and said connection means ensure the transfer of energy from the supply element to the active element.

4. Surgical instrument according to claim 3, wherein the energy supply means are electrical energy supply means.

5. Surgical instrument according to claim 3, wherein the energy supply means are pneumatic energy supply means.

6. Surgical instrument according to claim 1, wherein:

the active element is constituted by at least two elements interconnectable with each other in a sealed fashion, namely a head, and an irrigation connector, the supply means for supplying at least one second fluid being in communication with the irrigation connector, a rear portion of the head including connection means complementary to those of the supply element for ensuring a sealed connection with said supply element, and the supply channel for the first fluid being in communication with the head, when said head is connected to the supply element.

7. Surgical instrument according to claim 1, wherein the supply means for supplying at least one second fluid are constituted by at least one supply tube, secured to the active element, and in communication with an external fluid source.

8. Surgical instrument according to claim 7, wherein said supply tube is in communication with at least two other tubes each connected to an external source of fluid.

9. Surgical instrument according to claim 8, wherein the supply tube and said two other tubes meet adjacent the active element.

10. Surgical instrument according to claim 7, wherein the supply tube is provided with control means for the flowrate of the second fluid admitted to the active element.

11. Surgical instrument according to claim 7, wherein at least one of said other tubes is provided with control means for the flow rate of the second fluid admitted to the active element.

12. Surgical instrument according to claim 7, wherein the supply channel opens into a cavity, and the means for ensuring closure of said supply channel comprise a closure plug structured and configured to be received by said cavity.

* * * * *